United States Patent
Cho

[19]
[11] Patent Number: 5,913,681
[45] Date of Patent: Jun. 22, 1999

[54] TRAY MODELING SYSTEM AND ARTICULATOR FOR PRODUCING A DENTAL MODEL

[76] Inventor: Kyung Rok Cho, 22844 Cottage Ct., Apt. 104, Novi, Mich. 48375

[21] Appl. No.: 09/133,231

[22] Filed: Aug. 13, 1998

[51] Int. Cl.[6] .................................................. A61C 11/00
[52] U.S. Cl. ............................... 433/60; 433/34; 433/65
[58] Field of Search .................................. 433/60, 63, 65, 433/34

[56] References Cited

U.S. PATENT DOCUMENTS

| | | | |
|---|---|---|---|
| 2,619,725 | 12/1952 | Roeser | 433/60 |
| 3,916,524 | 11/1975 | Lystager . | |
| 4,200,981 | 5/1980 | Fine | 433/60 |
| 4,299,570 | 11/1981 | Yogosawa | 433/65 |
| 4,439,151 | 3/1984 | Whelan | 433/60 |
| 4,865,544 | 9/1989 | Scruggs | 433/64 |
| 5,197,874 | 3/1993 | Silva et al. | 433/74 |
| 5,306,145 | 4/1994 | Michael | 433/34 |
| 5,622,497 | 4/1997 | Cho | 433/60 |
| 5,658,143 | 8/1997 | Kuperman | 433/60 |

OTHER PUBLICATIONS

Dental Ventures of America, Inc. Brochure on "DVA Refractory Model System".

Vertex Price List & Order Form (Vertex/KV33 Dental Impression Model and Articulaor) Brochure for Nu. Logic— E–Z Tray Model System.

*Primary Examiner*—John J. Wilson
*Attorney, Agent, or Firm*—Gifford, Krass, Groh, Sprinkle, Anderson & Citkowski, P.C.

[57] ABSTRACT

An improved tray system and articulator for use with a replication of a dental patient's teeth taken by a conventional dental impression in the creation of a dental model of the patient's mouth. A first tray and a second tray are provided, each tray including a base surface, first and second spaced apart and upwardly extending side walls and first and second end walls. The side walls are each defined by pluralities of spaced apart and vertically extending raised portions which permit segmented portions of the upper and lower dental models to be releasably attachable in correct position. The articulator includes a first mounting portion extending from the first tray and a second identically shaped mounting portion extending from the second tray. A first insert portion engages the first mounting portion and a second insert portion engages the second mounting portion. The first and second insert portions are each adjustable in height relative to their associated trays and further include aligning eyelet portions which permit them to be hingedly secured along a common axis so as to provide for desired positioning of the opposingly arrayed dental models.

9 Claims, 3 Drawing Sheets

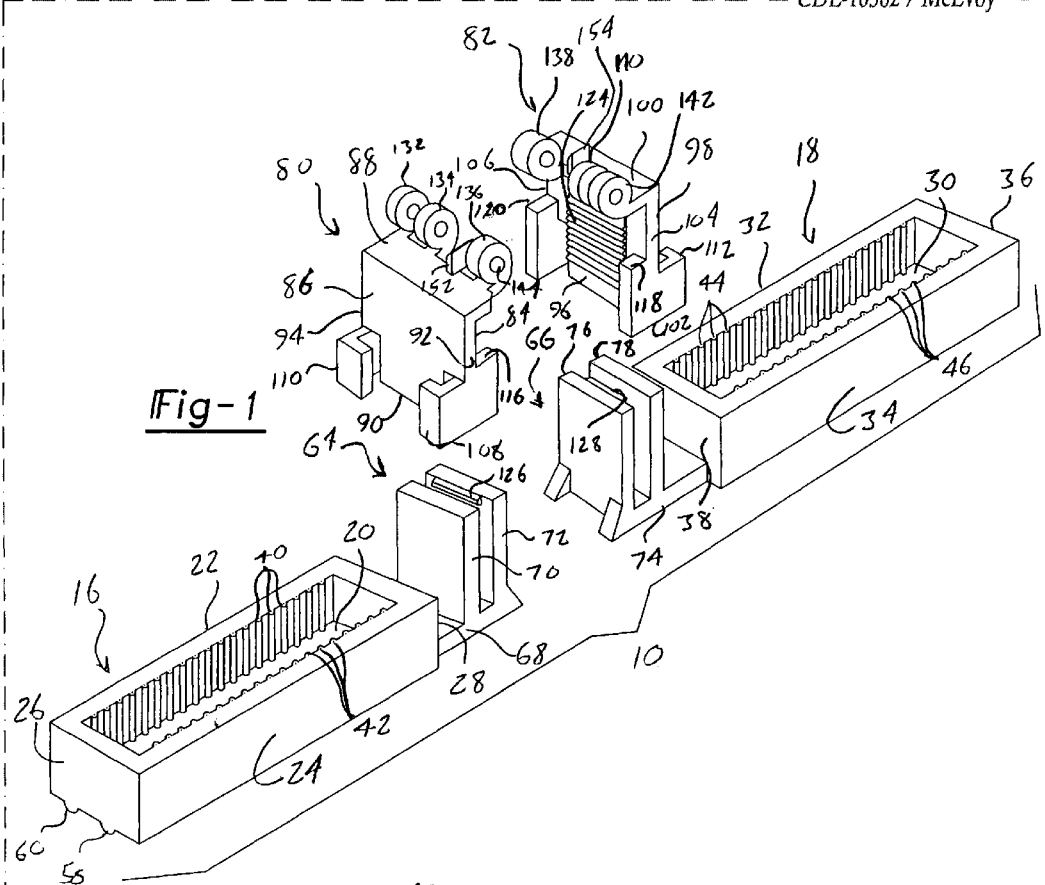

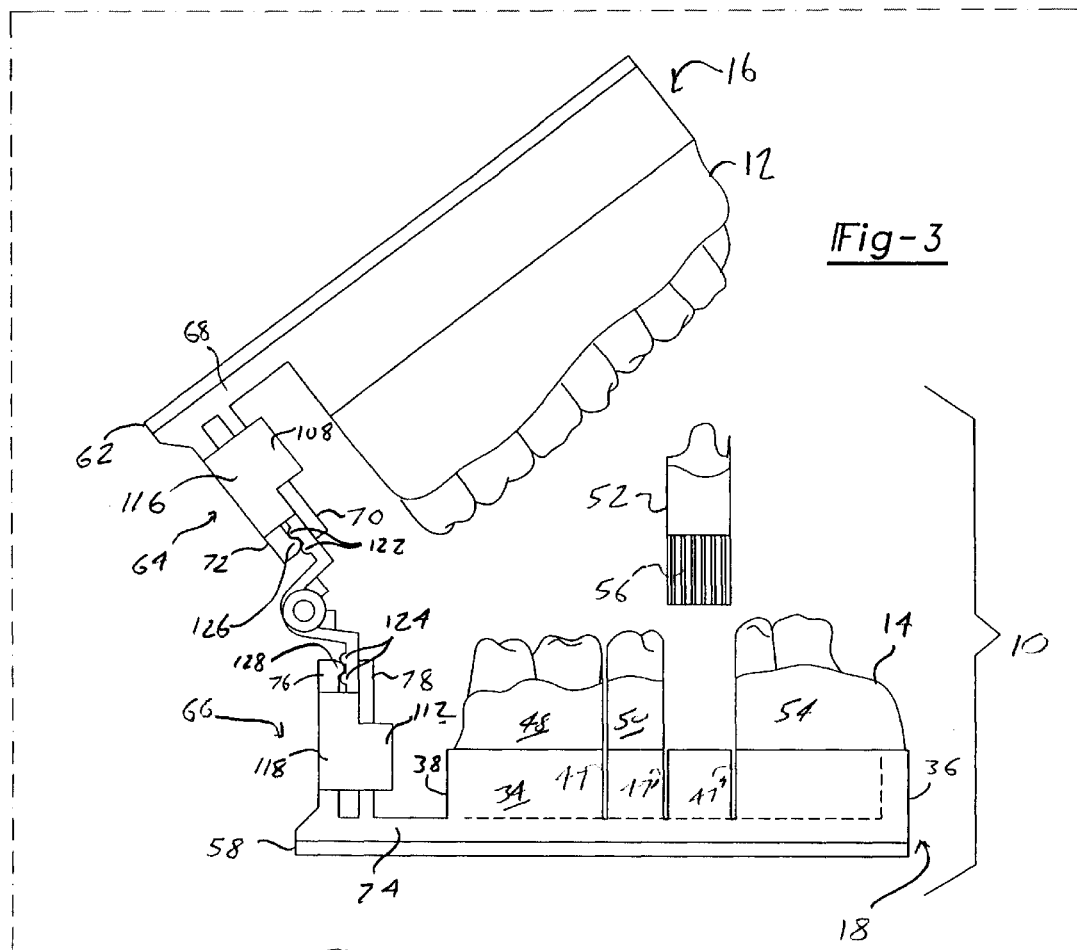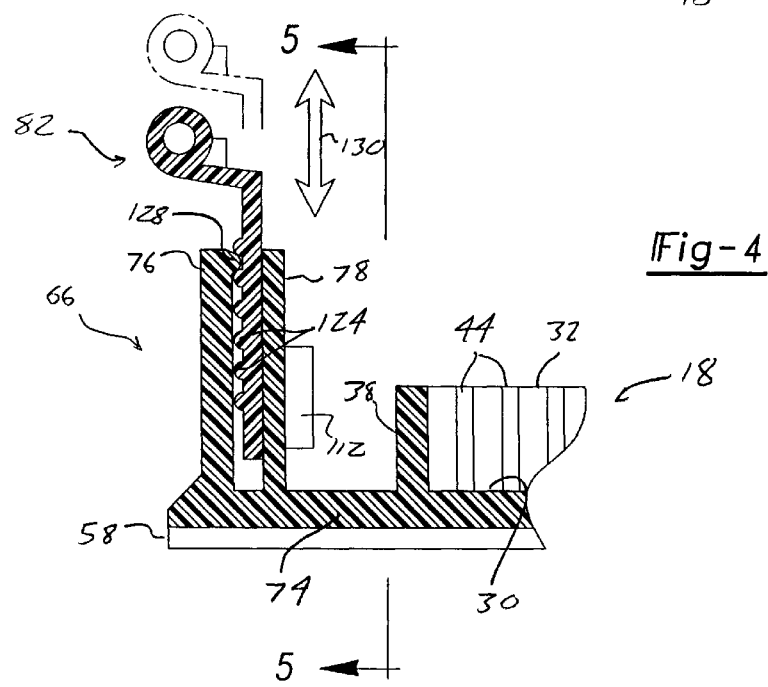

TRAY MODELING SYSTEM AND ARTICULATOR FOR PRODUCING A DENTAL MODEL

BACKGROUND OF THE INVENTION

1. Field of the Invention

The present invention relates generally to modeling devices for mounting teeth replications made from dental impressions to create a dental model of a patient's mouth and, more particularly, to an improved tray modeling system and articulator for producing such a dental model.

2. Description of the Prior Art

Numerous devices are known in the art for creating a working dental model of a patient's upper and lower teeth which are taken from dental impressions at the dentists office. The impression material is typically a malleable compound or a wax-type material which is molded around the patient's upper and lower teeth and gums and which creates a highly accurate negative impression of the teeth and surrounding areas. The impression is then filled with a powderized stone impression material or other appropriate material and is permitted to harden to form a highly accurate replication of the user's teeth. A series of metal dowel pins are inserted into the still hardening stone material which fills the impression at spaced intervals and correspond to the teeth or sections of teeth which are intended to be separated later on. The modeling device is normally engaged by the dowel pins to position and secure the dental impressions of the patient in such a manner so as to provide the dental professional with a highly accurate model of the user's mouth which will make possible the replication of certain of the patient's teeth in the preparation of dentures, crowns and the like.

The Vertex/KV 33 Corporation advertisement brochure teaches a dental impression model in which a powderized stone material similar to that used to create a conventional dental impression of the user's teeth is poured into an open mold. The stone material in the mold is allowed to harden to a certain degree, upon which a release spray coating is applied evenly over the exposed surface. The previously created dental impression is then immediately pressed into the mold base by engaging the dowel pins through the still somewhat malleable mold. The individual teeth or sections of teeth corresponding to the previously placed dowel pins may then be individually cut and separated from the stone base due to the release coating which prevents bonding of the hardening stone in the impression with that from the mold. The release coating allows the separated portions bonded around their respective dowel pins to be easily removed from the stone base and thus enables the specialist to begin preparing his or her model. An articulator, or universal mounting apparatus, is also employed to mount an upper impression model at a desired opposing orientation relative to a corresponding lower impression model to replicate the arrangement of the upper and lower rows of teeth.

While being fairly accurate in providing an accurate dental impression model, the Vertex model suffers from the shortcoming of being very time consuming to produce and necessitating a considerably large amount of stone substrate material, which again requires a considerable amount of setting time. An improvement of the Vertex device is taught by the Dental Ventures of America (DVA) model and die system which, in the place of a standard mold base, provides a predrilled base plate upon which the preformed dental impressions are attached. While the base plate of the DVA system reduces somewhat the time required to assemble the impression into the mold, the required time for producing the initial teeth replications from the impressions and the step of inserting the individual dowel pins into the hardening stone still largely offsets this advantage.

A marked improvement over the conventional impression models is provided by the Nu Logic E-Z Tray Model System which provides a collection of quarter and half trays which are shaped with cavities generally corresponding to the upper and lower impressions of the user's mouth and which define knurled ridges along both inwardly and outwardly facing edges which define the cavity. One or more keyed spine portions are snappingly engaged within groove shaped apertures formed in the bottom center and extending the length of the cavity. The keyed portion of the spine extends upwardly a distance into the cavity and, upon pouring of a quantity of the stone mix into the cavity, is bonded to the stone mix. The spines replace the conventional dowel pins and permit the impression and mold to be directly press fit onto the forming stone mix in the tray.

As further disclosed by the Nu Logic brochure, the model is separated from an overlaying dental impression which is press fit atop the drying stone in the base. The stone case with embedded spine may then be removed as an entire piece from the impression tray. The impression and spine may be cut by an appropriate saw into the desired sections of teeth which can then be remounted onto the tray by aligning the exterior knurled ridges of the stone case with the corresponding inwardly facing knurled ridges on the oppositely facing edges of the tray and then snapping the severed spine portions back in place along the guide slot formed in the bottom of the cavity.

U.S. Pat. No. 5,622,497, issued to Cho, discloses an improved tray system and articulator for use with a replication of a dental patient's teeth. First and second trays are provided, with each tray having a substantially planar surface upon which a substrate layer of a stone material is applied. An insert is detachably secured to each of the trays and includes an upper keyed portion around which the stone layer bonds. An upper conventional dental impression is secured to the substrate stone layer of the first dental tray and a lower dental impression is secured to the substrate layer of the second dental tray. The impression and substrate are secured to the upper and lower trays by removing the insert from within a channel formed within each tray. The channels extend around the peripheral outer portion of each tray and include first and second oppositely facing walls having rows of ridges placed thereon. Corresponding lower portions of the like configured insert are likewise provided with ridges or serrations to intermesh in an axially locating fashion at a selected point within the channel shaped tray recesses. A reusable articulator is also provided and includes first and second hinged members which secure to the first and second trays and mount the trays so as to position the teeth replications.

SUMMARY OF THE PRESENT INVENTION

The present invention is an improved tray system and articulator for use with a conventional dental impression for creating a dental model of a patient's mouth. The tray system includes in a first preferred embodiment first and second rectangular shaped trays for holding, respectively, upper and lower dental models. Each of the trays includes a base surface, first and second spaced apart and upwardly extending side walls, and first and second end walls which define in combination recessed cavities which extend the longitudinal length of the trays. The side walls of each of the trays each further include a plurality of spaced apart and vertically extending raised portions, the purpose for which is to provide for accurate repositioning of segmented portions of a dental model once they have been cut and removed from the tray.

The articulator includes first and second mounting portions extending from the first and second trays, respectively. The mounting portions include a base which supports first and second planar shaped and spaced apart guide portions for receiving therebetween first and second insert portions. The insert portions each include a plurality of horizontally disposed and alternating raised and recessed surfaces formed upon a specified planar surface which interengage in a biasing and height adjustable fashion with a further horizontally disposed and raised portion defined at an upper end of an opposing planar shaped guide portion. Pluralities of eyelet portions extend from a top of each of the insert portions and are twistingly and biasingly engaged together in a hingedly aligning fashion so as to form a common hinged axis.

In a further preferred embodiment, the trays are formed in a substantial U-shaped configuration for mounting respectively thereon a full upper half and a full lower half of a dental model. Reinforcing portions are further provided which extend from a rear of the base surface of each of the trays.

BRIEF DESCRIPTION OF THE DRAWINGS

Reference will now be had to the attached drawing, when read in combination with the following specification, wherein like reference numerals refer to like parts throughout the several views, and in which:

FIG. 1 is an exploded view in perspective of the tray modeling system and articulator according to a first preferred embodiment of the present invention;

FIG. 2 is an assembled view showing the tray system and articulator mounting upper and lower dental impressions of a patient's teeth and further illustrating the manner of segmenting portions of the dental model created according to the present invention;

FIG. 3 is a view similar to that shown in FIG. 2 and further illustrating the manner of removing segmented portions of the dental model according to the present invention;

FIG. 4 is a sectional view in side profile of the slidably connecting members forming a first half of the articulator according to the present invention;

DETAILED DESCRIPTION OF THE PREFERRED EMBODIMENT

Figure 5:
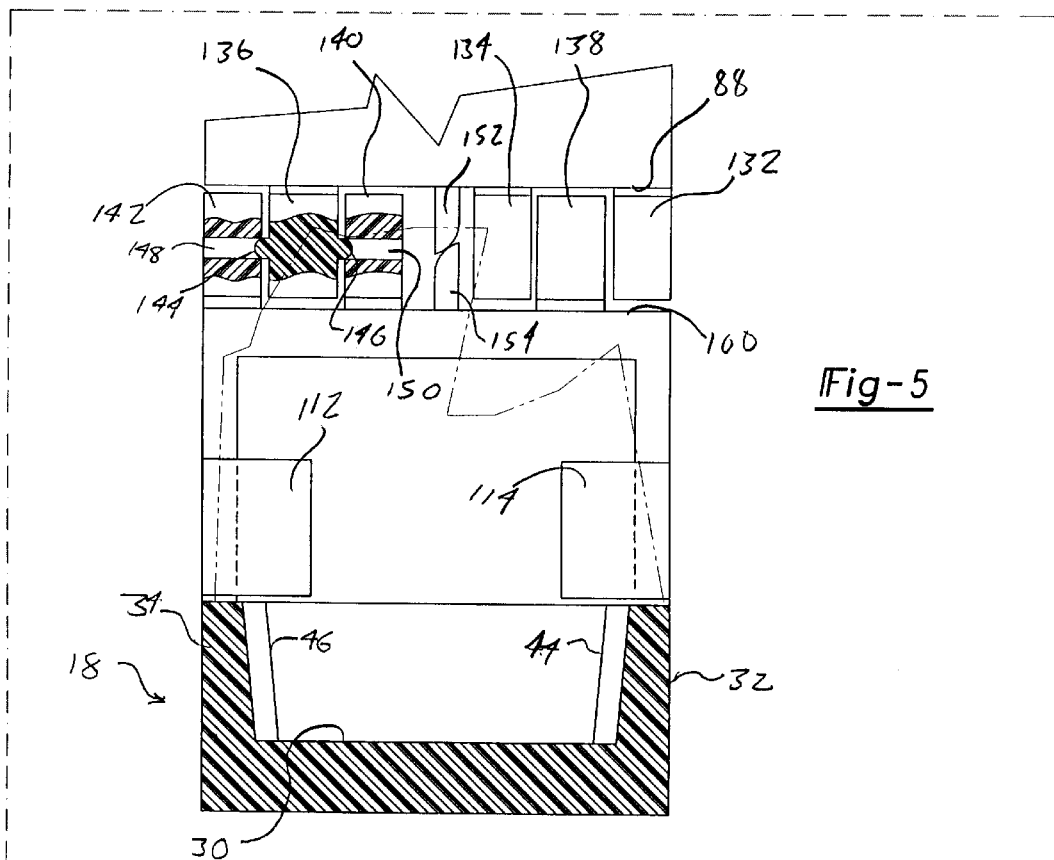
FIG. 5 is a cutaway view taken along line 5—5 of FIG. 4 and illustrating the hingedly connecting nature of the first and second articulator insert portions.

Referring now to FIGS. 1, 2 and 3, an improved tray system and articulator 10 is shown according to a first preferred embodiment for mounting teeth replications 12 and 14 produced by conventional dental impressions into a dental model of a patient's mouth. As was previously described, the taking of dental impressions at a dentists office is fairly well known in the art and normally involves fashioning a malleable and highly impressionable material such as a wax compound around the teeth and contours of the patients mouth. The dental impression is then used by a specialist along with X-rays taken by the dentist to construct a model of the patient's upper and lower teeth in a manner which will be subsequently described.

A first tray 16 and a second tray 18 are provided for mounting, respectively, the teeth replications 12 and 14. Both the first tray 16 and the second tray 18 are constructed of a polymer or like material and, as is illustrated in the first preferred embodiment, forms a generally rectangular shaped outline for mounting a quadrant (half of an upper or half of a lower) of a patient's dental model as are illustrated by dental replications 12 and 14. The first tray 16 includes a base surface 20, a first upwardly extending side wall 22, a second spaced apart and upwardly extending side wall 24, a first end wall 26 and a second end wall 28 which define in combination a recessed cavity extending a longitudinal length of the tray 16. Likewise, the second tray 18 includes a base surface 30, a first upwardly extending side wall 32, a second spaced apart and upwardly extending side wall 34, a first end wall 36 and a second end wall 38 and which also define in combination a recessed cavity extending a longitudinal length of the tray 18.

The side walls of the first and second trays each further include pluralities of spaced apart and vertically extending raised portions defined on inwardly facing surfaces. Specifically, side walls 22 and 24 of the first tray 16 include pluralities of spaced apart raised portions 40 and 42 while side walls 32 and 34 of the second tray 18 include pluralities of spaced apart raised portions 44 and 46. The purpose of the vertically extending raised portions 40, 42, 44 and 46 is to provide for an accurate locating means once portions of the teeth are segmented and are releasably attached to the dental model.

Referring especially to FIGS. 2 and 3, the stone material which forms the foundation of the upper and lower teeth replications 12 and 14 is filled within the recessed cavities of the first and second trays and in turn receives thereupon the previously created dental model from the impression. Referring to FIG. 2, a series of vertical cuts 47, 47' and 47" are made at desired locations as are shown and so as to segment the lower dental model 14 into sections 48, 50, 52 and 54. The cuts extend the height of the upwardly extending side walls (such as side walls 32 and 34 in FIGS. 2 and 3) and to an upper edge of the base surface 30. At this point any desired segmented section or sections of the dental replication 12 or 14 (in the case of FIG. 3 the section 52 of lower replication 14) is capable of being vertically removed from the tray 18 and subsequently resecured to the tray due to the spaced apart and raised portions defined on the side surfaces of the segment (again in this instance raised portions 56 on segment 52) which locate and reseat at the desired position relative to the raised portions defined on the interior facing surfaces of the tray side walls. Due to the closeness of the cuts to the bottom surface of the base of the trays, reinforcing portions are provided (as illustrated at 58 and 60 for tray 18 and at 62 for the side profile of tray 16) at spaced apart and longitudinally extending fashion along the bottom surface of the trays. The reinforcing portions assist in ensuring that the extent of the vertical cuts in the tray will not excessively weaken the integrity of the tray.

As an additional feature to safeguard the integrity of the dental model, a conventional adhesive 63 may be applied between the boundaries of the vertically cut sections 47, 47' and 47" to the upper edge of the upwardly extending side wall (see in FIG. 2 at side wall 34). By re-adhesively securing the cut boundaries, the sectioned teeth replications may still be releasably secured and, otherwise, would tend to wobble and deflect within the model.

The articulator according to the present invention includes a first mounting portion 64 and a second mounting portion 66 which extend, respectively, from a selected end wall of the associated tray. In the preferred embodiment, the mounting portions 64 and 66 are integrally formed with the associated tray 16 and 18 are constructed of a similar polymer or like material. The first mounting portion 64 includes a base 68 which supports first 70 and second 72 planar shaped and spaced apart guide portions. Likewise, the second mounting portion 66 includes a base 74 which supports first 76 and second 78 planar shaped and spaced apart guide portions.

The articulator further includes a first insert portion 80 and a second insert portion 82 which are capable of being received between the spaced apart pairs of planar shaped guide portions. Specifically, the first insert portion 80 includes a planar shaped body defined by a first planar surface 84, a second opposite facing planar surface 86 separated by a predetermined thickness, a top 88, a bottom 90, a first side 92 and a second side 94. The second insert portion 82 also includes a planar shaped body defined by a first planar surface 96, a second opposite facing planar surface 98 separated by a predetermined thickness, a top 100, a bottom 102, a first side 104 and a second side 106.

The insert portions 80 and 82 are illustrated in exploded fashion in FIG. 1 and in assembled fashion in FIGS. 2, 3 and 4 and further include guide portions extending from each of the first and second sides which encircle associated sides of a selected planar shaped and spaced apart guide portion. Specifically, the insert portion 80 includes angled guide portions 108 and 110 which encircle sides of the guide portion 70 of the first mounting portion 64. Correspondingly, the insert portion 82 includes identical angled guide portions 112 and 114 (see also FIG. 5) which encircle sides of the guide portion 78 of the second mounting portion 66. Additional stabilizing portions are illustrated at 116 for first insert portion 80 (the second being hidden from view in FIG. 1) and at 118 and 120 for second insert portion 82. The purpose of the additional stabilizing portions is to assist in locating the insert portions relative to the other of the planar shaped and spaced apart guide portions. Specifically, the stabilizing portions (116) of the first insert portion 80 overlap sides of the second planar shaped guide portion 72 of the first mounting portion 64 and the stabilizing portion 118 and 120 of the second insert portion 82 overlap sides of the second planar shaped guide portion 78 of the second mounting portion 66.

The articulator includes adjustment means established between the insert portions and the mounting portions which permit the insert portions to be raised or lowered a specified height relative to the mounting portions. The adjustment means includes a plurality of horizontally disposed and alternating raised and recessed surfaces, such as at 122 for first insert portion 80 and at 124 for second insert portion 82. The alternating raised and recessed surfaces 122 and 124 are defined upon a selected planar surface of the insert portions, such as upon surface 84 for first insert portion 80 and upon surface 96 for second insert portion 82. The opposing planar surfaces of the planar shaped guide portions relative to the alternating raised and recessed surfaces 122 and 124 include a horizontally disposed and raised portion defined at an upper end thereof and this is illustrated at 126 for planar shaped guide portion 72 and at 128 for planar shaped guide portion 76.

Reference is also made to FIG. 4, which illustrates the height adjusting capability of the insert portions relative to the mounting portions and shows a range of adjustment along two way directional line 130 of insert portion 82 relative mounting portion 66 of second tray 18. The height of the insert portions relative to the associated trays (as is illustrated for second tray 18 in the sectional view of FIG. 4) is determined by biasingly engaging the raised portions 128 within a selected recessed surface of the alternating raised and recessed surfaces 124 and the range of permitted adjustment is determined by the plurality of horizontally disposed raised and recessed surfaces.

Means are further provided for hingedly securing the first insert portion 80 and the second insert portion 82 together and includes a first plurality first 132, second 134 and third 136 eyelet portions extending from the top 88 of the first eyelet portion 80 and which are twistingly and biasingly engaged with a second plurality of first 138, second 140 and third 142 eyelet portions extending from the top 100 of the second insert portion 82. As is further best illustrated in FIG. 5, the engagement of the pluralities of eyelet portions along a common axis is better illustrated and a feature for providing the secure engagement is shown by the laterally projecting ends 144 and 146 (of eyelet portion 136) which seat within opposing circular recessed portions (identified at 148 and 150 for eyelet portions 142 and 140, respectively). Although illustrated schematically in FIG. 5, the identical hingedly securing means is employed for the other interengaging plurality of eyelet portions 134, 138 and 132. Also provided extending from the tops 88 and 100 of the insert portions 80 and 82 are first and second aligning tabs 152 and 154, the purpose for which is to facilitate correct aligning of the first and second pluralities of eyelet portions prior to said twisting engagement.

Figure 6:
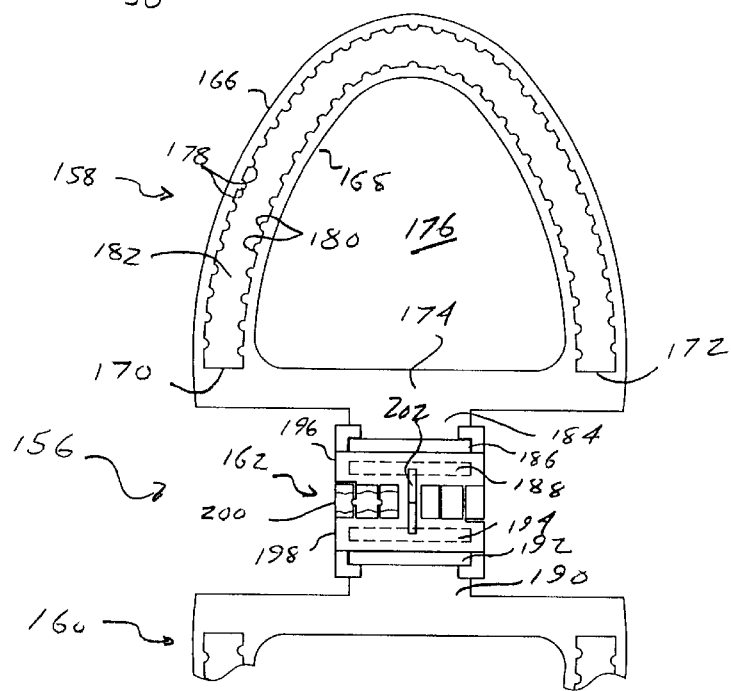
FIG. 6 is a view of full tray modeling system with articulator according to a further preferred embodiment of the present invention.

Referring now to FIG. 6, an improved tray assembly and articulator is illustrated according to a further preferred embodiment 156 of the present invention and includes a first substantially U-shaped configured tray 158 and a second (partially sectioned) and likewise U-shaped configured tray 160 which are hingedly interconnected by an articulator 162. The second tray 160 is identical in construction to the first tray 158 which includes an arcuate shaped body having a first outer extending side wall 166, a second spaced apart and inner extending side wall 168, a first end wall 170 and a second end wall 172. The end walls 170 and 172 are connected along a common edge 174 of the tray 158 and such that an interior 176 of the tray 158 is open to reduce material costs.

The first and second side walls 166 and 168 likewise include pluralities of spaced apart and vertically extending raised portions, see at 178 and 180, respectively as well as bottom surfaces, at 182 for the first tray 158, and which function in the same manner as previously illustrated for the embodiment of FIGS. 1–5 for providing for segmenting and accurate repositioning of portions of the dental replications. The construction of the dental trays 158 and 160 is such that they are capable of supporting thereon complete upper and lower dental models (including teeth and stone substrate) in the same fashion as illustrated in the previous embodiment.

The articulator 162 is illustrated in assembled and overhead unfolded fashion in FIG. 6 and the components of the articulator, including first mounting portion 184 with first planar shaped guide portion 186 and second planar shaped and spaced apart guide portion 188, as well as second mounting portion 190 with first planar shaped guide portion 192 and second planar shaped and spaced apart guide portion 194 are identical as to those disclosed in the first preferred embodiment. Also illustrated in overhead fashion are the first and second insert portions 196 and 198 with overlapping eyelet portions 200 and aligning tabs 202 which function to define a common hinged axis for the articulator 162.

The present invention according to either embodiment therefore discloses an improved tray modeling system with articulator which exhibits improved height adjustment capability of the trays relative to the articulators for providing more true to scale model replications of a patients teeth. Having described my invention, additional embodiments will become apparent to those skilled in the art to which it pertains without deviating from the scope of the appended claims.

I claim:

1. A tray system and articulator for use in creating a dental model of a patient's mouth, comprising:

a first tray and a second tray, said first tray supporting an upper dental model in an opposing and spatially arrayed fashion relative to a second tray which supports a lower dental model, said first and second trays each including a base surface, first and second spaced apart and upwardly extending side walls and first and second end walls, said side walls each further including a plurality of spaced apart and vertically extending raised portions, said side walls and said end walls defining a recessed cavity extending substantially a longitudinal length of each of said trays and which is suitable for receiving a base layer of stone, said associated dental model being bonded to said base layer of stone;

said articulator including a first mounting portion extending from said first tray and a second mounting portion extending from said second tray, a first insert portion engaging said first mounting portion and a second insert portion engaging said second mounting portion, each of said first and second mounting portions integrally formed with and extending from a selected end wall of said associated tray, said mounting portions each further including a base which supports first and second planar shaped and spaced apart guide portions for receiving said insert portions therebetween;

hinged securing means for pivotally connecting said first insert portion to said second insert portion; and adjustment means for establishing a height of each of said insert portions relative to said associated trays;

whereby portions of said upper and lower dental models are capable of being segmented and releasably attachable to said first and second trays in correct position due to said pluralities of raised portions, said adjustment means and said hingedly securing means providing for desired positioning of said opposingly arrayed dental models.

2. The tray system and articulator as described in claim 1, said first and second insert portions each further comprising:

a planar shaped body capable of being received between said first and second planar shaped guide portions of each of said mounting portions, said planar shaped body including first and second planar surfaces separated by a predetermined thickness, a top, a bottom, a first side and a second side;

guide portions extending from each of said first and second sides and encircling associated sides of a selected planar shaped and spaced apart guide portion;

said adjustment means further including a selected planar surface of said insert portion being defined by a plurality of horizontally disposed and alternating raised and recessed surfaces; and an opposing planar surface of a selected and planar shaped guide portion further including a horizontally disposed and raised portion defined at an upper end thereof;

whereby said height of said insert portions relative to said associated trays is established by biasingly engaging said raised portion within a selected recessed surface of said insert portion.

3. The tray system and articulator as described in claim 2, said hinged securing means further comprising a first plurality of first, second and third spaced apart eyelet portions extending from said top of said first insert portion, a second plurality of first, second and third spaced apart eyelet portions extending from said top of said second insert portion, said first and second pluralities of eyelet portions capable of being twistingly engaged in a hingedly aligning fashion so as to form a common hinged axis.

4. The tray system and articulator as described in claim 3, further comprising a first aligning tab extending from said top of said first insert portion and a second aligning tab extending from said top of said second insert portion, said aligning tabs facilitating correct aligning of said first and second pluralities of eyelet portions prior to said twisting engagement.

5. The tray system and articulator as described in claim 2, further comprising stabilizing portions extending from each of said first and second sides of said insert portions in opposite fashion relative said guide portions, said stabilizing portions overlapping associated sides of the other of said selected planar shaped and spaced apart guide portions.

6. The tray system and articulator as described in claim 1, said first and second trays each further comprising a rectangular shape for mounting respectively thereon an upper quadrant and a lower quadrant of a dental model.

7. The tray system and articulator as described in claim 1, said first and second trays each further comprising a substantially U-shape configuration for mounting respectively thereon a full upper half and a full lower half of a dental model.

8. The tray system and articulator as described in claim 1, further comprising said first and second spaced apart side walls being angularly outwardly configured in said upwardly extending direction.

9. The tray system and articulator as described in claim 1, further comprising reinforcing portions extending from a rear of said base surface of each of said trays along said longitudinal length.

* * * * *